United States Patent
Teo

[19]

[11] Patent Number: 5,876,343
[45] Date of Patent: Mar. 2, 1999

[54] METHODS AND APPARATUS FOR BLOOD SPECKLE DETECTION IN AN INTRAVASCULAR ULTRASOUND IMAGING SYSTEM

[75] Inventor: Tat-Jin Teo, Sunnyvale, Calif.

[73] Assignees: Scimed Life Systems, Inc., Maple Grove, Minn.; Boston Scientific Limited, Barbados, Barbados

[21] Appl. No.: 936,043

[22] Filed: Sep. 23, 1997

[51] Int. Cl.$^6$ ................................ A61B 8/00; A61B 8/12
[52] U.S. Cl. ............................................ 600/443; 600/467
[58] Field of Search ...................... 600/437, 443, 600/447, 451–458, 467, 463; 128/916; 382/6

[56] References Cited

U.S. PATENT DOCUMENTS

| | | | |
|---|---|---|---|
| 4,561,019 | 12/1985 | Lizzi et al. | 73/602 |
| 5,187,687 | 2/1993 | Burckhardt et al. | 367/7 |
| 5,224,483 | 7/1993 | Lipschutz | 128/662.02 |
| 5,363,849 | 11/1994 | Soursa et al. | 128/661.08 |
| 5,363,850 | 11/1994 | Soni et al. | 128/661.08 |
| 5,476,096 | 12/1995 | Olstad et al. | 128/660.07 |
| 5,479,926 | 1/1996 | Ustuner | 348/224 |
| 5,520,185 | 5/1996 | Soni et al. | 128/661.08 |
| 5,522,392 | 6/1996 | Suorsa et al. | 128/661.08 |
| 5,594,807 | 1/1997 | Liu | 382/128 |
| 5,664,572 | 9/1997 | Kishimoto | 600/443 |
| 5,720,291 | 2/1998 | Schwartz | 128/916 |

OTHER PUBLICATIONS

Entrechin, R. "Realtime Speckle Reduction in B–Mode Image", 1979 Ultrasonic Symposium pp. 169–174.

Gronningsaeter, Aage et al., "Blood Noise Reduction in Intravascular Ultrasound Imaging," *IEEE Transactions on Ultrasonics, Ferroelectrics and Frequency Control,* vol. 42, No. 2, Mar. 1995, pp. 200–209.

Foster, F.S. et al., "Ultrasound Backscatter From Blood in the 30 to 70 MHz Frequency Range," *1994 IEEE, 1994 Ultrasonics Symposium,* pp. 1599–1602.

Lockwood, G.R., et al., "Measurement of the Ultrasonic Properties of Vascular Tissues and Blood From 35–65 MHz," *Ultrasound in Med. & Biol.,* vol. 17, No. 7, pp. 653–666, 1991.

Shung et al., "Scattering of Ultrasound by Blood," *IEEE Transactions on Biomedical Engineering,* vol. BME–23, No. 6, Nov. 1976, pp. 460–467.

*Primary Examiner*—Francis J. Jaworski
*Attorney, Agent, or Firm*—Townsend and Townsend and Crew

[57] ABSTRACT

Methods and apparatus for blood speckle detection for enhanced intravascular ultrasound imaging. The present invention utilizes the fact that the energy scattering strength from blood exhibits a high frequency dependency, while the scattering strength from tissue lacks a strong frequency dependency. In specific embodiments, the present invention may provide a particularly simple and useful solution for addressing the problem of blood speckle in intravascular ultrasound imaging, especially in situations where the blood may have a scattering strength similar to that of tissue and/or where the blood is moving slowly or not at all.

20 Claims, 4 Drawing Sheets

5,876,343

METHODS AND APPARATUS FOR BLOOD SPECKLE DETECTION IN AN INTRAVASCULAR ULTRASOUND IMAGING SYSTEM

BACKGROUND OF THE INVENTION

The present invention relates to high resolution intravascular imaging and more particularly to intravascular ultrasound imaging and techniques for enhancing image quality.

In intraluminal or intravascular ultrasound (also referred to as "IVUS") imaging, the production of high resolution images of vessel wall structures requires imaging at high ultrasound frequencies. In some types of intraluminal systems, an ultrasonic unidirectional exciter/detector within a catheter probe positioned within a blood vessel is used to acquire signal data from echoes of the emitted ultrasonic energy off the interior of the blood vessel. Specifically, vectors are created by directing focused ultrasonic pressure waves radially from a transducer in a catheter and collecting echoes at the same transducer from the target area. A plurality of radial vectors from the rotated transducer comprises an image frame. A signal processor performs image processing (e.g., stabilization of a moving image, temporal filtering for blood speckle, and other image enhancement techniques) on the acquired data in order to provide a display of the corrected and filtered intravascular image on a rasterscan display monitor.

It is desirable to provide imaging over a broad range of frequencies (e.g., 5 Megahertz (MHz) to 50 MHz), especially higher ultrasonic frequencies in some applications. However, the backscatter from blood cells in such an image is a significant problem in high frequency intraluminal ultrasound imaging, since the scattering of ultrasound from blood cells is proportional to the fourth power of the frequency such that the higher the ultrasound frequency the more pronounced is the backscatter from blood. As a result, echoes from blood molecules degrade the lumen-to-vessel wall contrast, which is undesirable since there is a need to define the blood/tissue boundary in order to ascertain the degree of narrowing of the vessel and to determine the spatial extent of the plaque. Therefore, echoes in the ultrasound image due to backscatter from blood (the irregular pattern of backscatter from blood is referred to as "blood speckle") must be detected in order to provide an enhanced image display. Once detected, the blood speckle may be removed or suppressed to a level at which wall structures can be distinguished from blood, distinguished by providing a different display color for the blood, and/or used to better delineate the blood/tissue interface.

Various techniques have been used in intravascular ultrasound imaging for detecting blood speckle in the image. These techniques are not always effective in distinguishing between blood and tissue, because they are based on key assumptions which are not always true. Some techniques rely on the assumption that the energy scattering strength from blood is low in comparison to the scattering strength from tissue, in order to distinguish between blood and tissue. Other techniques rely on the assumption that the blood moves much faster compared to the tissue and thus has a different Doppler signal than the tissue. In reality, however, such assumptions may be violated. In particular, the energy scattering from blood can sometimes be equally as bright as the scattering from tissue, and/or blood may sometimes move with very low velocity or not be moving at all. Although generally effective, these techniques may not be so effective in situations when these assumptions are not valid.

From the above, it can be seen that alternative or supplementary methods and apparatus are needed for detecting blood speckle to allow a display of intraluminal ultrasound images to be free of or to distinctly identify blood-induced echoes.

SUMMARY OF THE INVENTION

The present invention provides methods and apparatus which detect blood speckle in an improved manner. The present invention utilizes the fact that the energy scattering strength from blood exhibits a high frequency dependency, while the scattering strength from tissue lacks a strong frequency dependency. In specific embodiments, the present invention may provide a particularly simple and useful solution for addressing the problem of blood speckle in intravascular ultrasound imaging, especially in situations where the blood may have a scattering strength similar to that of tissue and/or where the blood is moving slowly or not at all.

According to a specific embodiment, the present invention provides a method of detecting blood speckle in an intravascular ultrasound blood vessel image. The method includes the steps of illuminating an intravascular target with ultrasonic RF energy to generate ultrasonic echoes from the intravascular target, and transforming the ultrasonic echoes from the intravascular target into a received RF signal. The method also includes performing spectral analysis on at least a portion of the received RF signal to provide intensity information on the spectrum of the received RF signal. The information includes a first intensity strength at a high frequency within the spectrum and a second intensity strength at a low frequency within the spectrum. The method further includes comparing the first intensity strength and the second intensity strength, and determining that the intravascular target is tissue if the first intensity strength and the second intensity strength are approximately equal and that the intravascular target is blood if the first intensity strength is greater than the second intensity strength. This determining step takes into account strength sensitivities at the high and low frequencies. Some specific embodiments may perform spectral analysis either by complete Fourier analysis or by filtering for the high and low frequencies.

According to another specific embodiment, the present invention provides a method of detecting blood speckle in an intravascular ultrasound blood vessel image that includes the steps of illuminating an intravascular target with ultrasonic RF energy at a first frequency to generate ultrasonic echoes from said intravascular target to form a first image frame, and illuminating the intravascular target with ultrasonic RF energy at a second frequency to generate ultrasonic echoes from the intravascular target to form a second image frame. The first and second image frames are successive in time and one of the first and second frequencies is a low frequency with the other one being a high frequency. The method also includes step of subtracting the first and second image frames to obtain a subtracted image frame and the step of determining that portions of the subtracted image frame that are substantially cancelled-out are tissue and that portions of the subtracted image frame that are not cancelled-out are blood. The determining step takes into account strength sensitivities at the high and low frequencies.

According to yet another specific embodiment, the present invention provides an apparatus for an ultrasonic blood vessel imaging system. The apparatus includes a transducer having a frequency bandwidth including known and sufficiently high strength sensitivities at a first frequency and a second frequency. The transducer obtains echoes from an intravascular target using ultrasounds transmitted at the first and second frequencies to form an intravascular image. The first and second frequencies are between a −3 dB low frequency and a −3 dB high frequency of the transducer. The apparatus also includes a signal processing device and a computer-readable medium. The signal processing device is capable of being coupled to the transducer and to a display for displaying the intravascular image. Coupled to be read by the signal processing device, the computer-readable medium stores a computer-readable program for comparing a first intensity strength for echoes from ultrasound at the first frequency with a second intensity strength for echoes from ultrasound at the second frequency to detect blood speckle in the intravascular image.

These and other embodiments of the present invention, as well as its advantages and features, are described in more detail in conjunction with the text below and attached figures.

DESCRIPTION OF THE SPECIFIC EMBODIMENTS

The present invention provides for the accurate discrimination between blood and tissue for enhanced image processing in intravascular ultrasound imaging systems. The present invention may use spectral analysis to distinguish blood from tissue, according to specific embodiments. In particular, the present invention utilizes the fact that the energy scattering strength from blood (i.e., blood cells, which are on the order of about 2 micrometer ($\mu$m) thick and about 7 $\mu$m diameter, are particles much smaller than the wavelength of the ultrasound energy) exhibits a high frequency dependency, while the scattering strength from tissue lacks a strong frequency dependency. That is, for scattering due to blood, the scattering intensity at higher frequencies is much stronger than the energy scattering at lower frequencies. Since the spectrum provides information on any frequency dependency that may exist, examining the spectrum can provide information about the size of the reflectors to indicate whether the reflectors are blood or tissue.

Figure 1A:
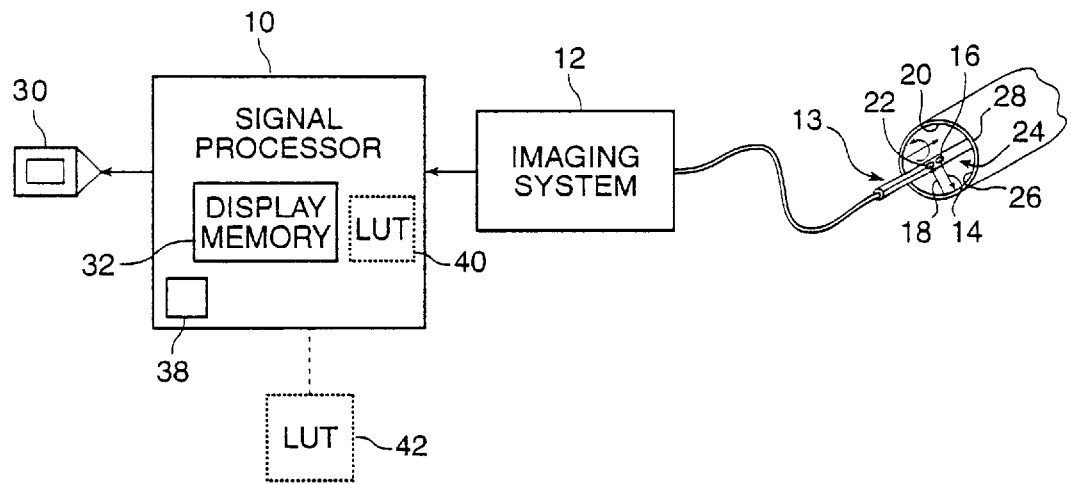
FIG. 1A is a block diagram of an intravascular ultrasonic imaging system in accordance with specific embodiments of the invention.

The present invention provides image processing methods which may be used in conjunction with the intravascular ultrasonic imaging system shown in FIG. 1A. Referring to FIG. 1A, there is shown a block diagram of a type of intravascular ultrasonic imaging system 10 that may be used for intravascular image display in accordance with the invention. As seen in FIG. 1A, a specialized signal processing device 10 is used with an ultrasonic imaging system 12 including a catheter probe 13 wherein ultrasonic beams 14 are emitted by an ultrasonic transmitter or exciter 16. The ultrasonic signals 14 of, for example, 5 MHz to 50 MHz, are directed to an intravascular target to cause reflections in the form of ultrasonic echo signals 18 from the intravascular structures, including blood. Radial spokes or vectors 18 of information are collected from a target 20 (the interior walls of a blood vessel) based on ultrasonic reflections at a transducer 22. Specifically, information is gathered by projecting narrow ultrasonic sampling beams 14 from exciter 16 as it is rotated (by an angle $\theta$) within catheter 13 within blood vessel 20. The reflections scale in amplitude over a range and are recorded by transducer 22 as amplitude as a function of unit distance (r) along the radius of each vector. A total of, for example, 256 spokes radially directed from the catheter 13 is sufficient to obtain data for an image frame to process the information according to a specific embodiment of the present invention. This image data acquisition may provide either analog or digital information, depending on the specific system utilized. The data acquired is converted into pixels representing points in a scanned (swept or rotated) two-dimensional image are assigned a value on, for example, a gray scale between black and white. Of course, colors may be assigned in other embodiments. The image is representative of a cross-sectional "slice" of the structure of blood vessel 20 and includes wall structures (blood-wall interface) 26 and lumens of blood (blood region) 24, as seen in FIG. 1A. More specifically, after the intravascular ultrasonic imaging system acquires the image data, signal processor 10 performs signal processing of the acquired image data by scan-converting the image data into x-y rasterized image data for storing into display memory 32 and then stabilizing the rasterized image data on a frame-by-frame basis to provide the raster image for viewing on a display device 30 coupled to signal processor 10. Signal processor 10 also includes a program memory 38 which may be used to store the computer-readable program(s) for implementing specific embodiment(s) of the present invention, as discussed further below. Alternatively, the computer-readable program(s) for implementing specific embodiments of the present invention may be stored on a memory coupled to signal processor 10. For example, the memory may be a read-only memory, fixed disk drive, or removable disk drive. The present invention can be used to distinguish or suppress/remove blood speckle in the displayed image.

Figure 1B:
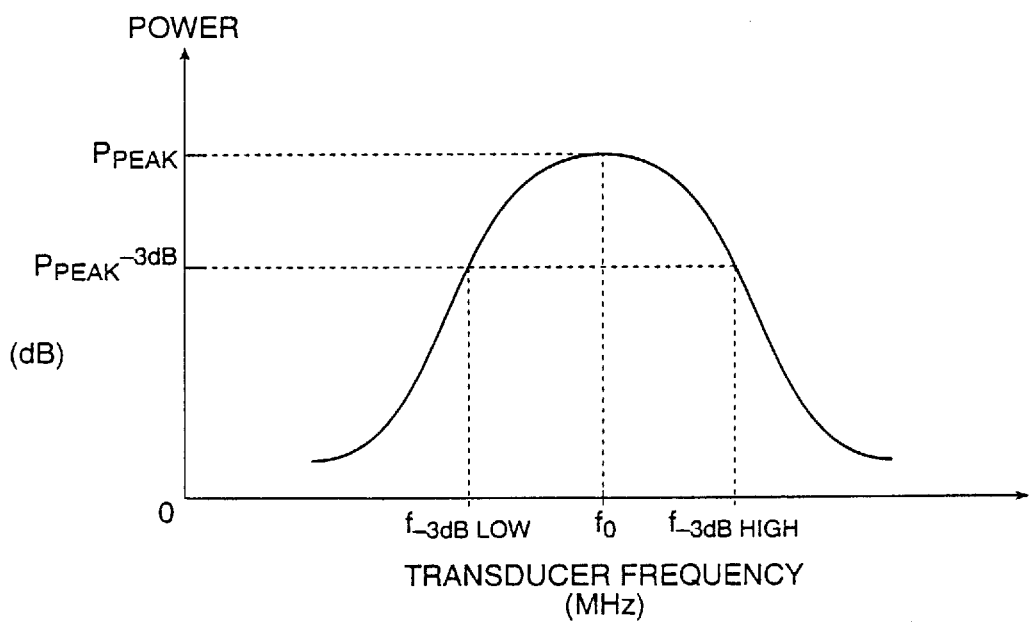
FIG. 1B is a simplified diagram of the power sensitivity of a transducer as a function of frequency, in accordance with specific embodiments of the invention.
Figure 2:
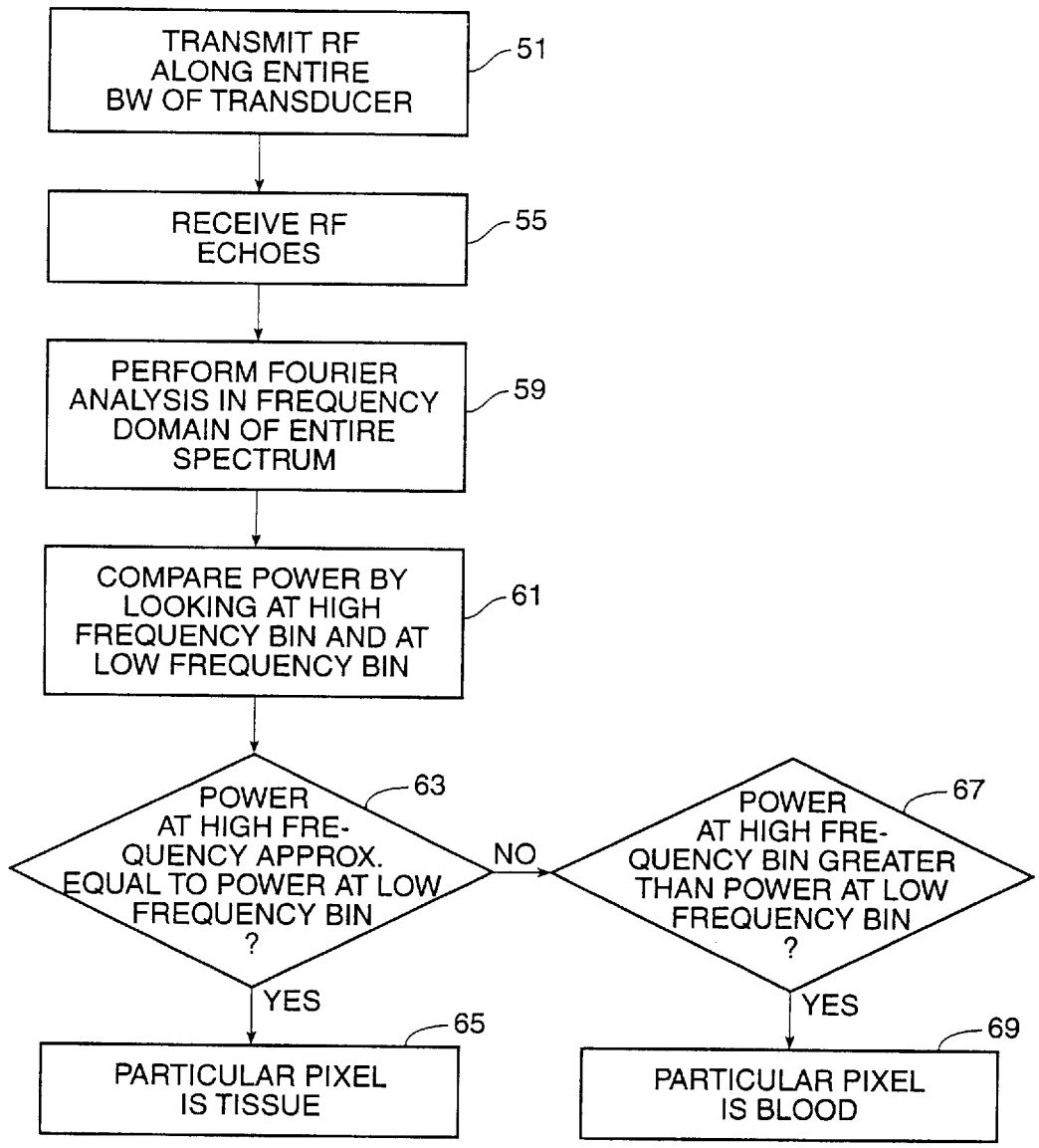
FIG. 2 is a simplified flow diagram illustrating a specific embodiment that analyzes the entire spectrum to distinguish between blood and tissue.

According to a specific embodiment of the present invention, the radio frequency (RF) of the echoes would be acquired and then analyzed in the frequency domain using Fourier analysis to compute the spectrum, as is well known in the art. FIG. 2 is a simplified flow diagram illustrating a specific embodiment that analyzes the entire spectrum. It is noted that the associated electronics of the apparatus in order to acquire the RF echoes would have to deal with a higher frequency as well as have a higher dynamic range compared to apparatus used with an approach which acquires the log-compressed envelope of the reflected echoes. According to this specific embodiment, the transducer transmits RF along its entire bandwidth (indicated as step 51) and receives RF echo signals (step 55). Computed using Fourier analysis (step 59), the power spectrum of the RF echo signals characterizes the nature of the reflectors to provide information for better distinguishing between blood and tissue. In this specific embodiment, after the RF is acquired and spectral analysis is performed, the strength of the received RF signal at the two frequency bins are compared. In particular, the strength of the spectrum in two frequency bins (a higher frequency bin and a lower frequency bin) where the transducer has known sensitivities are examined. Specifically, this embodiment requires the use of a transducer with a wide bandwidth which includes a lower frequency bin and a higher frequency bin having substantially well known and sufficiently high sensitivities. As shown in FIG. 1B, which is a simplified diagram of the power sensitivity of a transducer (the transducer has a center frequency $f_0$ at which the transducer has a peak power, $P_{PEAK}$) as a function of frequency, both the higher and lower frequency bins are preferably selected to fall within the range between the −3 dB low frequency $f_{-3dB\ LOW}$ (the frequency below $f_0$ at which power is half of $P_{PEAK}$) and the −3 dB high frequency $f_{-3dB\ HIGH}$ (the frequency above $f_0$ at which power is half of $P_{PEAK}$). In a preferred embodiment, the higher and lower frequency bins are both selected to fall within the range between the −3 dB low frequency $f_{-3dB\ LOW}$ and $f_0$. However, in alternative embodiments, the higher and lower frequency bins may be selected to fall within the range between $f_0$ and the −3 dB high frequency $f_{-3dB\ HIGH}$. In another alternative embodiment, for example, the lower frequency bin may be selected to fall within the range between the transducer's center frequency $f_0$ (the frequency at which the transducer has a peak power, $P_{PEAK}$) and the −3 dB low frequency $f_{-3dB\ LOW}$ (the frequency below $f_0$ at which power is half of $P_{PEAK}$), and the higher frequency bin may be selected to fall within the range between the transducer's center frequency $f_0$ and the −3 dB high frequency $f_{-3dB\ HIGH}$ (the frequency above $f_0$ at which power is half of $P_{PEAK}$). The two frequency bins should also be selected to be as separate as possible from each other (so that the bandwidths of each frequency bin do not overlap or are not too close to each other) without falling out of the range of the transducer's frequencies with known and sufficiently high sensitivities. For example, for frequency bins selected close to the center frequency, more narrowband frequency bins should be used. For frequency bins selected further away from the center frequency, wider band frequency bins may be used as long as the bins remain within the −3 dB frequencies. A comparison of the strength of the spectrum at those two frequency bins (taking into account the particular strength sensitivities at each bin) determines whether the echoes were reflected from tissue or from blood. If the strength of the spectrum at those two frequencies is approximately equal (taking into account the known sensitivities of the transducer at each frequency bin) as indicated in step 63, then the echoes were reflected from tissue and the particular pixel is determined to be tissue (indicated by step 65). If the higher frequency bin has a greater strength than the lower frequency bin (also taking into account the known sensitivities of the transducer at each frequency bin) as indicated in step 67, then the reflected echoes came from blood and the particular pixel is determined to be blood (step 69). This embodiment performs an analysis of the entire spectrum with the steps shown in FIG. 2 being performed for each radial spoke and the comparison of strength for the high and low frequency bins being performed for each sampling point in the radial spoke. In an exemplary implementation of this specific embodiment, the transducer has a center frequency of about 40 MHz with about a total 20 MHz bandwidth, and the analysis and examination of the entire spectrum would be computation-intensive, as a complete Fourier analysis is involved. This specific embodiment may be desirable in some applications, since the information obtained (such as or including the spectral analysis for the entire spectrum) may be useful for other purpose in addition to detecting blood speckle.

Figure 3:
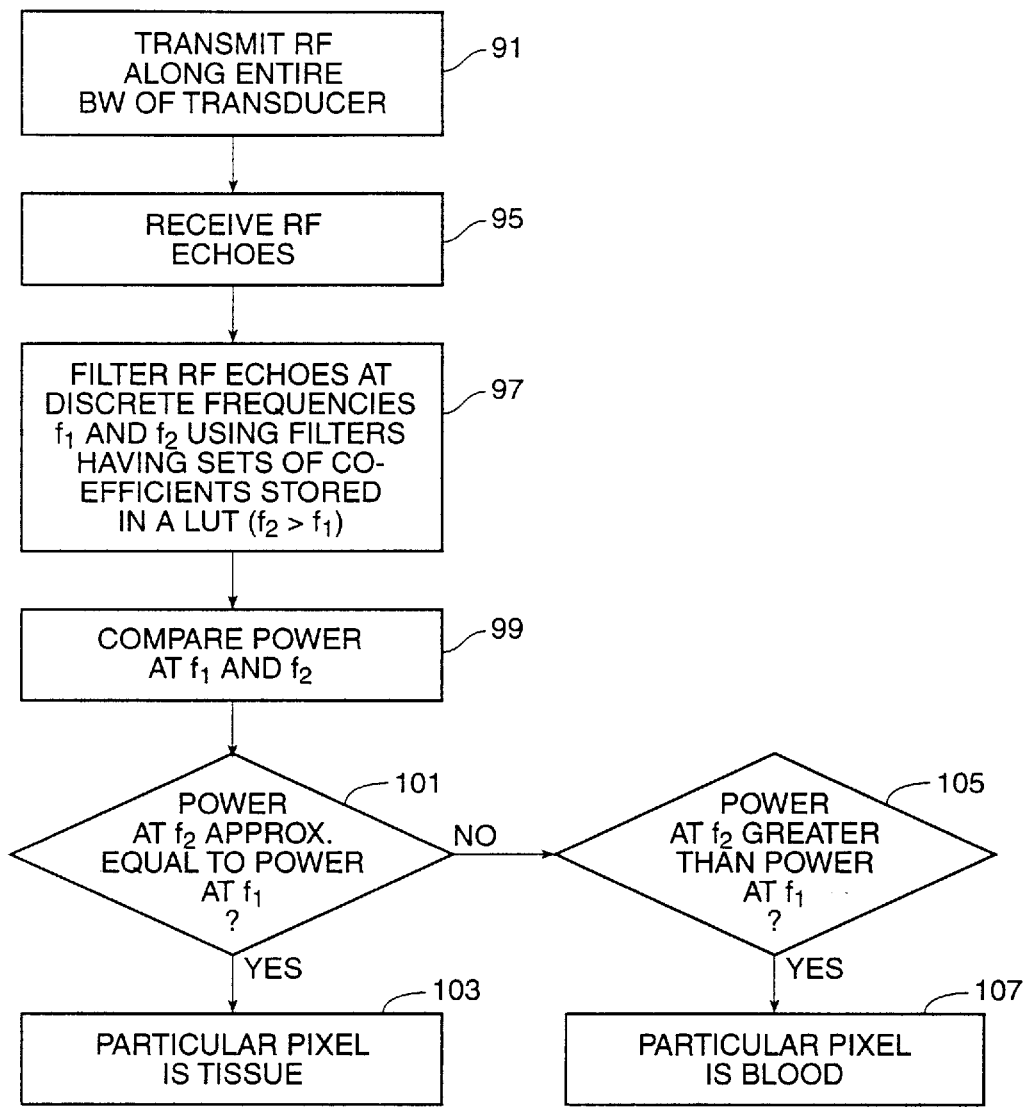
FIG. 3 is a simplified flow diagram illustrating another specific embodiment that performs spectral analysis at only two discrete frequencies to distinguish between blood and tissue.

In another specific embodiment, the spectral analysis may be performed at two predetermined discrete frequencies for the transducer in the catheter. FIG. 3 is a simplified flow diagram illustrating the specific embodiment that performs spectral analysis at only two discrete frequencies. It is noted that this embodiment also requires the use of a transducer with a wide bandwidth which includes a lower frequency $f_1$ and a higher frequency $f_2$ at which the transducer has substantially well known and sufficiently high sensitivities, as discussed above for FIG. 1B. The two frequencies are selected to have known sensitivities for the particular transducer in the catheter and to fall within the preferred frequency range (between the −3 dB high and low frequencies, as discussed above). The following discussion also assumes that the strength comparison at the two discrete frequencies takes into account the known sensitivities of the transducer at the respective frequencies, in a similar manner as discussed for the embodiments of FIG. 2. According to this specific embodiment, the transducer transmits RF along its entire bandwidth (indicated as step 91) and receives RF echo signals (step 95). In the present embodiment, spectral analysis is performed without having to perform Fourier analysis of the RF signal to provide the entire spectrum. Instead, the spectral analysis is performed (step 97) at the two discrete frequencies, lower frequency $f_1$ and a higher frequency $f_2$, by bandpass filtering. In one specific embodiment, the bandpass filtering is performed with a respective set of coefficients that are available through a look-up table (LUT), which may be included in (e.g., LUT 40 shown in dotted line in FIG. 1A) or coupled to (e.g., LUT 42 shown in dotted line in FIG. 1A) the signal processor 10 of FIG. 1A. In another specific embodiment, the bandpass filtering may be performed using hardware bandpass filters in imaging system 12 at each of the lower and higher frequencies. These embodiments thus avoid the need to do a complete Fourier analysis of the RF echo signal. A comparison (step 99) of the strength at those two discrete frequencies determines whether the echoes were reflected from tissue or from blood in the present embodiment, in a similar manner as the embodiment described in FIG. 2. That is, if the strength of the spectrum at those two frequencies is approximately equal (indicated in step 101), then the echoes were reflected from tissue and the particular pixel is determined to be tissue (indicated by step 103). If the higher frequency $f_2$ has a greater strength than the lower frequency $f_1$ (indicated in step 105), then the reflected echoes came from blood and the particular pixel is determined to be blood (step 107). This embodiment performs a spectral analysis and intensity-based comparison of the received RF signal at the two frequencies with the steps shown in FIG. 3 being performed for each radial spoke and the comparison of strength at the high and low frequencies being performed for each sampling point in the radial spoke. In an exemplary implementation, the transducer has a center frequency of about 40 MHz with about a total 20 MHz bandwidth and the apparatus may have lower processing and memory requirements, since the present embodiment is less computation-intensive by avoiding a complete Fourier analysis of the entire spectrum of the RF signal.

It should be noted that although exemplary implementations discussed for the previous two specific embodiments may use wideband transducers with a center frequency of about 40 MHz with about 20 MHz bandwidth, other types of transducers may be used in other exemplary implementations. As examples, wideband transducers having a center frequency/bandwidth range as follows may be used: about 9 MHz with about 3.6–5.4 MHz bandwidth; about 12 MHz with about 4.8–7.2 MHz bandwidth; or 30 MHz with about 12–18 MHz bandwidth. Other wideband transducers with even higher center frequencies, such as a transducer of about 100 MHz with about 40–50 MHz bandwidth, may be used, as long as the higher frequency or frequency bin used for the above two specific embodiments have corresponding wavelengths that are greater than the typical diameter (about 7 μm) of blood cells. It is noted that the transducer mounted in a catheter used in IVUS imaging systems currently provide information to the image processor through its catheter ID. Such information includes the center frequency of the particular transducer, and additional information that may be provided can include the −3 dB high frequency and the −3 dB low frequency, and/or the entire sensitivity power spectrum of the particular transducer, which may be used in accordance with the present invention.

Figure 4:
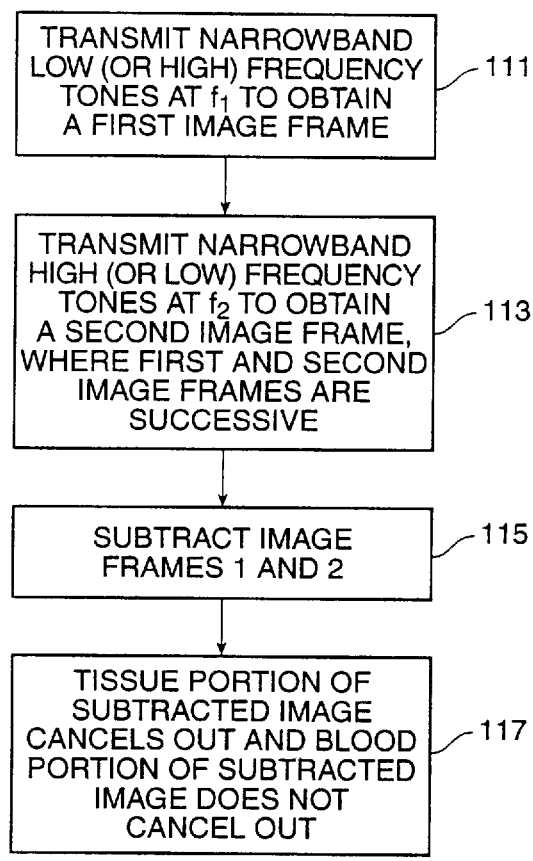
FIG. 4 is a simplified flow diagram illustrating a further specific embodiment that utilizes a high frequency and a low frequency to obtain two successive image frames used to distinguish between blood and tissue.

In still another specific embodiment, the need to perform spectral analysis and the need for a wide bandwidth transducer are eliminated, as explained further below. In the present specific embodiment, a wide bandwidth transducer may be used and the high frequency and the low frequency channels used with the wide bandwidth transducer may be wide bandwidth (i.e., shorter pulses) which are sufficiently separated from each other but within the range of −3 dB high and low frequencies, to account for known and sufficiently high sensitivities of the transducer. However, the present embodiment also allows for the use of a narrow bandwidth transducer where the high frequency and the low frequency channels used with the narrow bandwidth transducer have narrower bandwidths (i.e., longer pulses) which are sufficiently separated from each other but outside the range of −3 dB high and low frequencies, to account for known sensitivities of the transducer. FIG. 4 is a simplified flow diagram illustrating this specific embodiment that utilizes a high frequency and a low frequency to obtain two successive image frames used to distinguish between blood and tissue. In this specific embodiment (described for a narrow bandwidth transducer for simplicity), the transducer can transmit two narrowband tones at the two frequencies (high and low), where the transducer has known and sufficiently high sensitivities for the two frequency tones. As indicated by step 111, the transducer transmits a narrowband low frequency tones at $f_1$ to obtain a first image frame. Then, the transducer transmits a narrowband high frequency tones at $f_2$ to obtain a second image frame (step 113). As mentioned earlier, a plurality of radial vectors from the rotated transducer comprises an image frame. Of course, in other embodiments, the first image frame may be obtained by using a high frequency tone or channel and the second image frame may be obtained by using a low frequency tone or channel, as long as the successive image frames are obtained by a high frequency tone and a low frequency tone. The two successive images are subtracted in step 115. As indicated by step 117, the tissue portion would be largely cancelled and the blood portion would not, due to the fact that the reflected echoes' strengths between the two tones' frequencies would be similar for tissue and different for blood. The subtracted image information may then be used, for example, as a mask for removing blood speckle in the displayed image. Of course, this embodiment would incur the time to obtain two image frames for determining the blood's spatial distribution. In this embodiment, the bandwidth of each channel may be in the kilohertz (kHz) range with the channels separated from each other as much as possible but having both channels within the range of known sensitivities of the transducer, as discussed above for FIG. 1B. It should be recognized that the above discussion for this embodiment also assumes that the known sensitivities of the transducer at the high and low frequency tones are taken into account, in a similar manner as discussed for the embodiments of FIG. 2 with respect to the known sensitivities.

Because the present invention utilizes RF digitization, better digitization is required (i.e., more samples are required) so that not only are the signals' envelope detected but also individual signals need to be detected so that the analysis can be narrowed down. For some specific applications where transducers with $f_0$ of lower frequencies such as 10 MHz are required, direct sampling digitization may be used; whereas, known techniques for higher RF digitization may be utilized for specific applications where transducers with $f_0$ of higher frequencies such as 40 MHz are required.

The present invention may be used as the sole means for blood speckle detection, or as an adjunct for conventional intensity-based and motion-based analysis for blood speckle detection used to delineate the lumen and vessel wall boundary. Accordingly, the present invention provides an improved capability for detecting blood for applications such as assigning a distinct color to the detected blood in the displayed image, or suppressing or removing completely the detected blood from the displayed image. While the invention has been particularly shown and described with reference to preferred embodiments thereof, it will be understood by those skilled in the art that the foregoing and other changes in the form and details may be made therein without departing from the spirit or scope of the invention. It is therefore not intended that this invention be limited, except as indicated by the appended claims.

What is claimed is:

1. A method of distinguishing tissue from blood in an intravascular ultrasound blood vessel image, said method comprising the steps of:

illuminating an intravascular target with ultrasonic RF energy to generate ultrasonic echoes from said intravascular target;

transforming the ultrasonic echoes from the intravascular target into a received RF signal;

performing spectral analysis on at least a portion of said received RF signal to provide intensity information on the spectrum of said received RF signal, said information including a first intensity strength at a high frequency within said spectrum and a second intensity strength at a low frequency within said spectrum;

comparing said first intensity strength and said second intensity strength;

determining that said intravascular target is tissue if said first intensity strength and said second intensity strength are approximately equal and that said intravascular target is blood if said first intensity strength is greater than said second intensity strength, wherein said determining step takes into account tissue and blood backscatter strength sensitivities at said high and low frequencies.

2. The method of claim 1 wherein said step of performing spectral analysis is achieved by performing a complete Fourier analysis on said received RF signal such that said information provided is for the entire spectrum.

3. The method of claim 2 wherein a transducer used for said illumination step has known and sufficiently high detection sensitivities at both said high and low frequencies and wherein said low and high frequencies are selected to be between a low −3 dB frequency and a high −3 dB frequency of said transducer.

4. The method of claim 1 further comprising the step of:

selecting a narrowband high frequency channel containing said high frequency and a narrowband low frequency channel containing said low frequency.

5. The method of claim 4 wherein a transducer used for said illumination step has known and sufficiently high detection sensitivities at both said narrowband high and low frequency channels, and wherein said narrowband high frequency channel and said narrowband low frequency channel are selected to be between a low −3 dB frequency and a high −3 dB frequency of said transducer.

6. The method of claim 4 wherein a transducer used for said illumination step has known and sufficiently high detection sensitivities at both said narrowband high and low frequency channels, and wherein said narrowband high frequency channel and said narrowband low frequency channel are selected to be between a center frequency and a high −3 dB frequency of said transducer.

7. The method of claim 1 wherein said step of performing spectral analysis is achieved by filtering at said high frequency and at said low frequency.

8. The method of claim 7 wherein said filtering is performed by using respectively appropriate sets of filter coefficients stored in a memory such that said information provided is for said high frequency and for said low frequency.

9. The method of claim 8 wherein said filtering is performed using a look-up table as said memory.

10. The method of claim 7 wherein said filtering is performed by using hardware bandpass filters for said high frequency and for said low frequency.

11. The method of claim 1 wherein said illuminating step is performed with a transducer having a center frequency and a bandwidth of about 40–60% of said center frequency, wherein said high frequency is a frequency having a corresponding wavelength that is greater than the typical diameter of blood cells.

12. The method of claim 1 further comprising the steps of:

assigning said intravascular target a selected first shade if said first intensity strength and said second intensity strength are determined to be approximately equal and a selected second shade if said first intensity strength is determined to be greater than said second intensity strength; and providing said intravascular ultrasound blood vessel image with tissue having said selected first shade and blood having said selected second shade on a display.

13. The method of claim 1 wherein said selected second shade is selected such that said blood is suppressed or removed from said intravascular ultrasound blood vessel image on said display.

14. A method of distinguishing tissue from blood in an intravascular ultrasound blood vessel image, said method comprising the steps of:

illuminating an intravascular target with ultrasonic RF energy at a first frequency to generate ultrasonic echoes from said intravascular target to form a first image frame;

illuminating said intravascular target with ultrasonic RF energy at a second frequency to generate ultrasonic echoes from said intravascular target to form a second image frame, wherein said first and second image frames are successive in time and wherein one of said first and second frequencies is a low frequency and another one of said first and second frequencies is a high frequency;

subtracting said first and second image frames to obtain a subtracted image frame;

determining that portions of said subtracted image frame that are substantially cancelled-out are tissue and that portions of said subtracted image frame that are not cancelled-out are blood, wherein said determining step takes into account tissue and blood backscatter strength sensitivities at said high and low frequencies.

15. The method of claim 1 wherein a transducer used for said illumination steps has known and sufficiently high detection sensitivities at both said high and low frequencies, and wherein said high frequency is selected to be between a center frequency and a high −3 dB frequency of said transducer, and said low frequency is selected to be between the center frequency and a low −3 dB frequency of said transducer.

16. The method of claim 15 further comprising the steps of:

assigning said portions of said subtracted image frame that are not cancelled-out a selected shade; and providing said intravascular ultrasound blood vessel image with blood having said selected shade on a display, said selected shade being different from other shades for non-blood in said display.

17. The method of claim 15 further comprising the steps of:

providing said intravascular ultrasound blood vessel image on said display such that said portions of said subtracted image frame that are not cancelled-out are suppressed or removed from said intravascular ultrasound blood vessel image.

18. Apparatus for an ultrasonic blood vessel imaging system comprising:

a transducer having a frequency bandwidth including known and sufficiently high strength sensitivities at a first frequency and a second frequency, said transducer obtaining echoes from an intravascular target using ultrasounds transmitted at said first and said second frequencies to form an intravascular image, wherein said first and second frequencies are between a −3 dB low frequency and a −3 dB high frequency of said transducer;

a signal processing device capable of being coupled to said transducer and to a display for displaying said intravascular image;

a computer-readable medium storing a computer-readable program, said computer-readable medium coupled to be read by said signal processing device, said computer-readable program for comparing a first intensity strength for echoes from ultrasound at said first frequency with a second intensity strength for echoes from ultrasound at said second frequency to detect blood speckle in said intravascular image.

19. The apparatus of claim 18 wherein said computer-readable program compares said first and second intensity strengths for the same image frame.

20. The apparatus of claim 18 wherein said computer-readable program compares said first intensity strength with said second intensity strength by subtracting a first image frame obtained from echoes from ultrasound at said first frequency with a second image frame obtained from echoes from ultrasound at said second frequency to provide a subtracted image frame, said second image frame and said first image frame are successive image frames, said subtracted image frame including portions of said subtracted image frame that are not cancelled-out, said portions being deleted from or distinctly shaded in said intravascular image on said display.

* * * * *